United States Patent [19]
Egan

[11] Patent Number: 6,106,545
[45] Date of Patent: Aug. 22, 2000

[54] SUTURE TENSIONING AND FIXATION DEVICE

[75] Inventor: Thomas D. Egan, Marblehead, Mass.

[73] Assignee: Axya Medical, Inc., Beverly, Mass.

[21] Appl. No.: 09/061,472

[22] Filed: Apr. 16, 1998

[51] Int. Cl.$^7$ ................................................ A61B 17/04
[52] U.S. Cl. ............................................................ 606/232
[58] Field of Search .............................. 606/232, 72, 73, 606/233, 151, 155, 157, 212; 623/13

[56] References Cited

U.S. PATENT DOCUMENTS

| | | | |
|---|---|---|---|
| 1,669,537 | 5/1928 | Schaffer | 606/232 |
| 5,527,341 | 6/1996 | Gogolewski et al. | 606/232 |
| 5,593,425 | 1/1997 | Bonutti et al. | 606/232 |
| 5,735,877 | 4/1998 | Pagedas | 606/232 |
| 5,769,894 | 6/1998 | Ferragamo | 623/13 |

*Primary Examiner*—Michael Buiz
*Assistant Examiner*—Vikki Trinh
*Attorney, Agent, or Firm*—McDermott Will & Emery

[57] ABSTRACT

A suture tensioning and fixation device comprises a suture thread and a suture retaining element. The retaining element has a first suture thread engaging portion on the first end, a second suture thread engaging portion opposite the first suture thread engaging portion, and a third, substantially centrally located suture thread engaging portion. The retaining element is adapted such that segments of the suture thread can be interwoven between the suture thread engaging portions of the retaining element. The suture thread engaging portions of the retaining element are adapted to frictionally hold the interwoven segments of suture thread. Localized melting of the retaining element where it contacts the suture thread segments establishes a weld and bonds the suture thread to the retaining element in a knotless joint.

14 Claims, 3 Drawing Sheets

SUTURE TENSIONING AND FIXATION DEVICE

FIELD OF THE INVENTION

The invention relates to surgical devices used for suture fastenings.

BACKGROUND OF THE INVENTION

In the surgical repair of soft tissue, such as, for example, the surgical reattachment of ligaments to bone or the attachment of tendon to muscle, it is known to use multi-part devices to surgically fasten the soft tissues to be repaired. By way of example, U.S. Pat. No. 5,593,425 to Bonutti et al. discloses surgical devices assembled using heat bondable material. The '425 patent teaches that a portion of a suture thread is inserted into an opening in a retainer formed of a plastic material. At least one portion of the retainer is heated to its melting point. The plastic material of the retainer flows around the suture thread and creates a bond with the suture thread as the plastic material cools below its melting point.

Often these surgical procedures are performed endoscopically. Endoscopic procedures typically require the surgeon to perform the procedure through a very small opening which requires particular dexterity. One disadvantage of the device disclosed by the '425 patent is that the surgeon must maintain tension on the retainer while simultaneously heat bonding the retainer to the suture, a sometimes difficult procedure.

It would therefore be an advantage to provide a device that would hold the suture thread when the suture thread is pulled taut through the device. Thus, the surgeon would not have to simultaneously maintain tension on the retainer while heat bonding the retainer to the suture thread because the retainer holds the suture thread and maintains tension when the suture thread is pulled taut. This device, therefore, better enables the surgeon to perform surgical procedures through the small openings typically encountered in endoscopic procedures.

SUMMARY OF THE INVENTION

According to one aspect of the present invention, there is provided a suture tensioning and fixation device used for suture fastening of tissues. The device comprises a suture thread and a suture retaining element. The retaining element has a first suture thread engaging portion on the first end, a second suture thread engaging portion opposite the first suture thread engaging portion, and a third substantially centrally located suture thread engaging portion.

The retaining element is adapted such that segments of the suture thread can be interwoven between the suture thread engaging portions of the retaining element. The suture thread engaging portions of the retaining element are adapted to frictionally hold the interwoven suture thread segments.

The retaining element and the suture thread can be bonded together upon the application of energy, such as thermal or ultrasonic energy, thereto. In a preferred embodiment, the retaining element and suture are made of plastic materials. The retainer material preferably has a melting point which is lower than the melting point of the suture thread. Heat applied to the retainer melts the retaining element. The melted plastic flows around the suture, binding or fixing the suture in place upon cooling. In a preferred embodiment, the suture thread has a braided construction to provide interstices for the melted retainer material to flow into.

While any method of heating known to those skilled in the art is suitable, the retaining element is preferably melted via application of ultrasonic energy.

In another preferred embodiment, the substantially centrally located suture thread engaging portion of the retaining element is channeled or grooved or otherwise adapted to retain the suture thread.

BRIEF DESCRIPTION OF THE DRAWINGS

The invention is further described by the following description and figures, in which.

Like elements in the respective FIGURES have the same reference numbers.

DETAILED DESCRIPTION OF THE PREFERRED EMBODIMENTS

Figure 1:
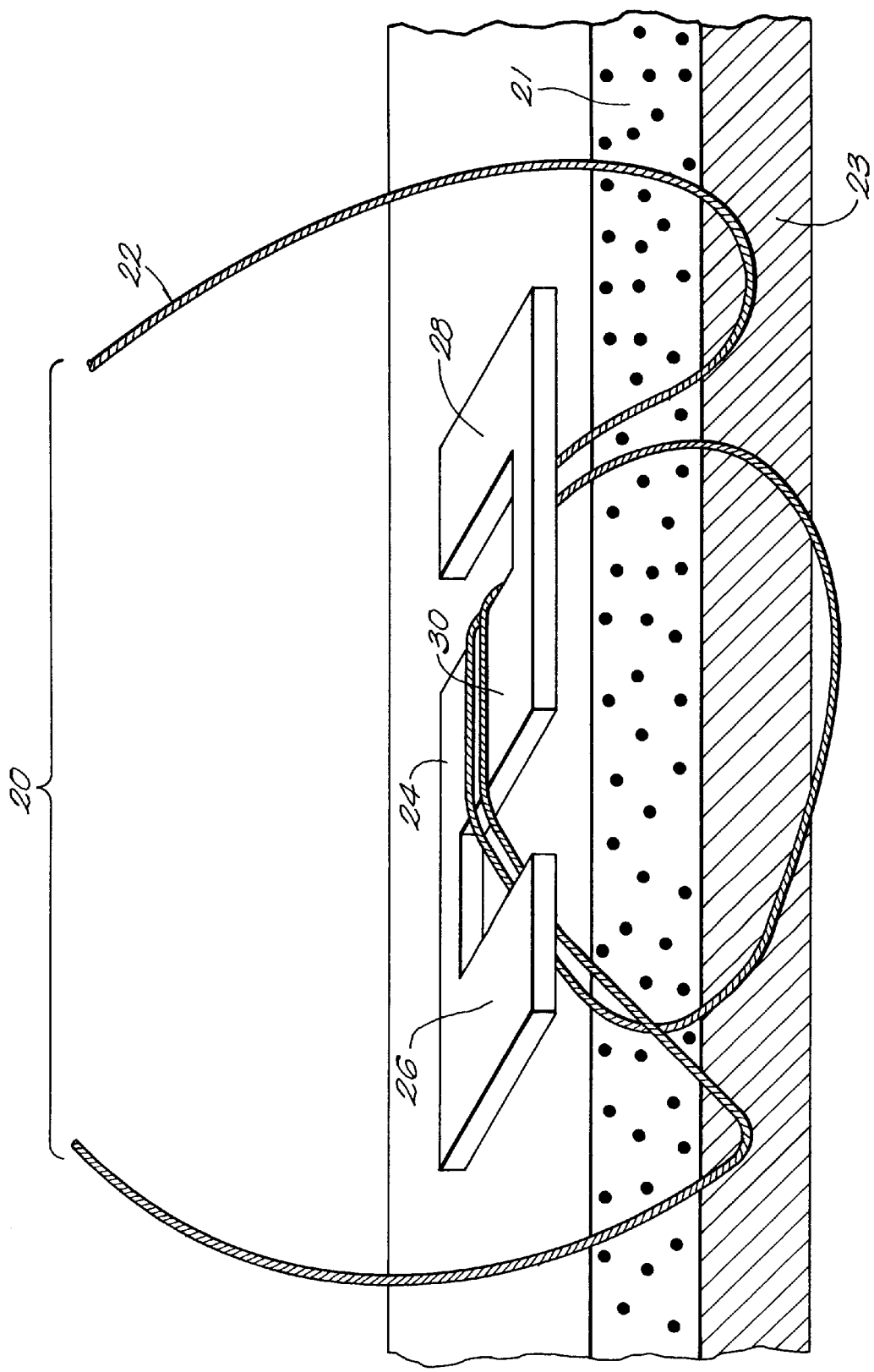
FIG. 1 is a perspective view of the suture tensioning and fixation device according to one embodiment of the the present invention, in which the suture retaining element has a serpentine shape.

The suture tensioning and fixation device according to the present invention is illustrated in FIG. 1. The device 20 comprises a suture thread 22 and a retaining element 24. The retaining element 24 is comprised of a first suture thread engaging portion 26, a second suture thread engaging portion 28 and a third suture thread engaging portion 30, located substantially centrally between the first suture thread engaging portion 26 and the second suture thread engaging portion 28. This embodiment has a serpentine shape which permits convenient passage of suture thread segments around the suture thread engaging portions.

Figure 2:
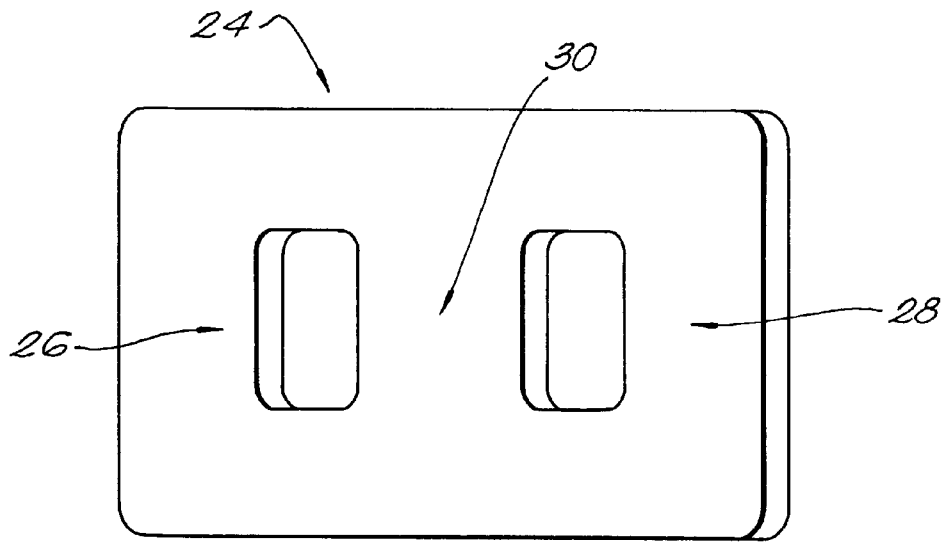
FIG. 2 is a perspective view of another embodiment of the retaining device of the present invention, in the shape of a figure 8.

A perspective view of the retaining element 24 according to one preferred embodiment of the present invention is shown in FIG. 2. In this embodiment the retaining element 24 is in the shape of a figure 8.

The retaining element may have any shape which is suitable for frictionally binding the suture thread. The serpentine shape is desirable because it allows the surgeon to more easily feed the suture thread into the retaining element. In another embodiment, the preferred shape of the retaining element is a figure 8. This embodiment is desirable because the suture thread cannot slip laterally from the retaining element.

Figure 3:
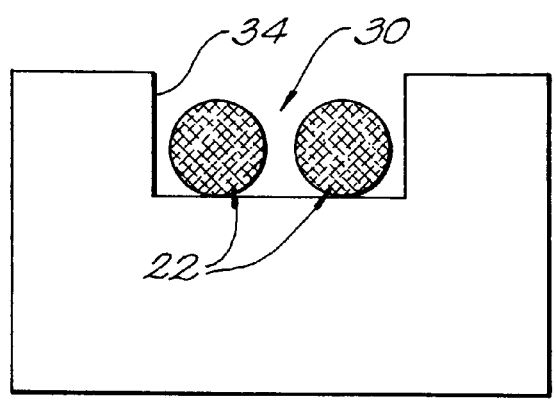
FIG. 3 is a cross-sectional view of one preferred embodiment of the device in which the centrally located suture engaging portion has a channel to receive and retain one or more segments of the suture thread.

FIG. 3 shows a cross-sectional view of the third centrally located suture thread engaging portion 30 of the retaining element 24. The third suture engaging portion 30 has a void region or channel 34 adapted to receive the suture thread 22.

Figure 4:
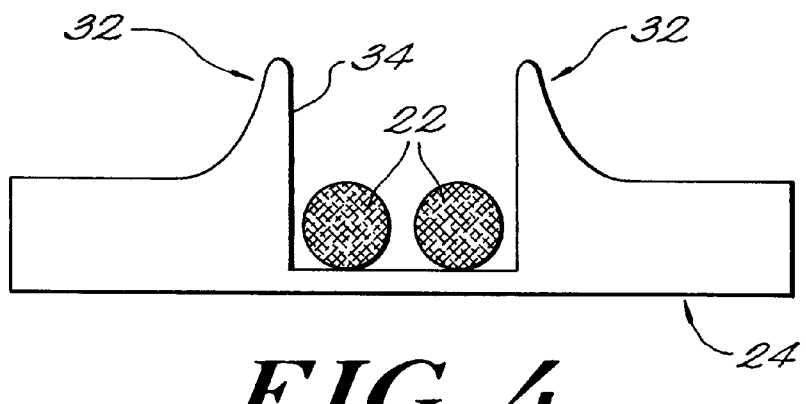
FIG. 4 is a cross-sectional view of one preferred embodiment of the device in which the suture engaging portion has a plurality of projecting tabs to receive and retain one or more segments of the suture thread.

FIG. 4 illustrates a cross-sectional view of another preferred embodiment of the third suture thread engaging portion 30 of the suture tensioning and fixation device 24. The third suture engaging portion 30 has a plurality of projecting tabs 32 at the sides of the channel 34. The tabs receive and retain the suture thread 22 within the channel 34 and are easily contacted by an ultrasonic welding horn or a heat source to melt them around the suture.

According to the present invention, the suture thread 22 is threaded, for example, through two segments of tissue 21 and 23 to be surgically fixed, as shown in FIG. 1. Segments of the suture thread 22 are then interwoven between the first suture thread engaging portion 26, the second suture thread engaging portion 28, and the third suture thread engaging portion of the retaining element 24, as shown in FIG. 1. The ends of the suture thread 22 are preferably tucked under the first and second suture engaging portions 26 and 28 of the retaining element to hold them in place. The suture thread is pulled taut and is frictionally held in place by the first, second, and third suture thread engaging portions 26, 28, 30, in preparation for bonding of the retaining element to the suture thread.

The retaining element and the suture thread are preferably heat bondable. In this embodiment, the retaining element and the suture may be made of a plastic material. The retaining element preferably has a melting point which is lower than the melting point of the suture thread. The suture may be a braided structure to provide interstices for receiving the melted material of the retaining element. Energy is then applied in the form of ultrasonic or thermal energy, which melts the retaining element. The melted plastic flows around the suture, binding or fixing the suture in place upon cooling. No knot is required to fix the suture in place. After the suture has been heat bonded, any excess segments of suture thread may be cut off.

Any method of heating known to those skilled in the art is suitable to heat and melt the plastic material of the retaining element. These include a hot air gun, a small welding or soldering gun, and ultrasonic wands. Preferably, however, the retaining element is melted by application of ultrasonic energy through an ultrasonic weld horn 38 and anvil 40, shown in FIG. 5.

Figure 5:
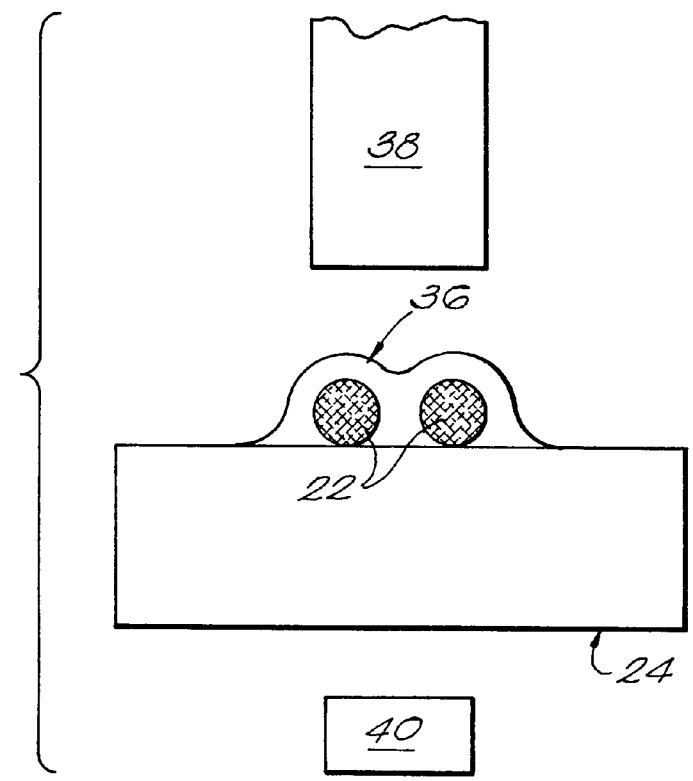
FIG. 5 is a cross-sectional view of FIG. 4 after the retaining element has been bonded to the suture.

FIG. 5 illustrates the retaining element 24 of FIG. 4 in which projecting tabs 32 are fused to the suture thread after application of ultrasonic energy to the tabs 32. The melted material 36 flows around the suture threads 22 and into the interstices of the suture threads to form a permanent bond when cooled.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

I claim:

1. A suture tensioning and fixation kit, comprising:

a. a suture thread; and b. a suture retaining element having a first suture thread engaging portion on one end of the retaining element, a second suture thread engaging portion opposite the first suture thread engaging portion, and a third, substantially centrally located, suture thread engaging portion; said suture retaining element being a substantially planar sheet for frictionally engaging suture thread;

wherein segments of the suture thread can be interwoven between the suture thread engaging portions, wherein the retaining element is heat bondable to the suture thread.

2. The device according to claim 1, wherein the retaining element is a plastic material having a melting point lower than the melting point of the suture thread.

3. The device according to claim 1, wherein the centrally located suture engaging portion of the retaining element includes one or more channels for the suture thread.

4. The device according to claim 3, wherein the centrally located suture engaging portion of the channel includes one or more projecting tabs.

5. The device according to claim l, wherein the retaining element has a serpentine shape.

6. The device according to claim 1, wherein the retaining element has a figure eight shape.

7. The device according to claim 1, wherein the suture thread is a braided suture thread.

8. A suture tensioning and fixation kit, comprising:

a suture retaining element having a first suture thread engaging portion on one end of the retaining element, a second suture thread engaging portion opposite the first suture thread engaging portion, and a third, substantially centrally located, suture thread engaging portion; said suture retaining element being a substantially planar sheet for frictionally engaging a suture thread;

wherein segments of the suture thread can be interwoven between the suture thread engaging portions, wherein the retaining element is heat bondable to the suture thread.

9. The device according to claim 8, wherein the retaining element is a plastic material having a melting point lower than the melting point of the suture thread.

10. The device according to claim 8, wherein the centrally located suture engaging portion of the retaining element includes one or more channels for the suture thread.

11. The device according to claim 10, wherein the centrally located suture engaging portion of the channel includes one or more projecting tabs.

12. The device according to claim 8, wherein the retaining element has a serpentine shape.

13. The device according to claim 8, wherein the retaining element has a figure eight shape.

14. The device according to claim 8, wherein the suture thread is a braided suture thread.

* * * * *